United States Patent [19]
Pollard et al.

[11] Patent Number: 5,738,212
[45] Date of Patent: Apr. 14, 1998

[54] FIBROUS PAD AND A DISPENSING PACKAGE THEREFOR

[75] Inventors: Ricky Alan Pollard, Moscow; Charles John Berg, Jr., Cincinnati, both of Ohio

[73] Assignee: The Procter & Gamble Company, Cincinnati, Ohio

[21] Appl. No.: 725,449

[22] Filed: Oct. 4, 1996

[51] Int. Cl.$^6$ .................................................. B65D 83/10
[52] U.S. Cl. ........................ 206/362; 206/210; 206/555; 15/208
[58] Field of Search ....................... 206/362, 581, 206/210, 823, 570, 555, 449; 15/208, 209.1, 244.1, 244.4

[56] References Cited

U.S. PATENT DOCUMENTS

| | | | |
|---|---|---|---|
| 1,820,256 | 8/1931 | Stewart | 15/244.4 |
| 1,822,725 | 9/1931 | Cooper et al. | 15/244.4 |
| 4,159,772 | 7/1979 | Beck . | |
| 4,517,702 | 5/1985 | Jackson | 15/244.1 |
| 4,769,267 | 9/1988 | Hoyt | 15/244.4 |
| 4,927,064 | 5/1990 | Burgin . | |

*Primary Examiner*—Paul T. Sewell
*Assistant Examiner*—Nhan T. Lam
*Attorney, Agent, or Firm*—Vladimir Vitenberg; Larry L. Huston; E. Kelly Linman

[57] ABSTRACT

A fibrous pads package comprises a lightweight dispensing package having a dispensing opening and a plurality of discrete fibrous pads sequentially disposed in the dispensing package in an abutting relationship with each other. Each of the plurality of fibrous pads comprises a cleansing portion and a gripping portion of a predetermined size and shape. Each of the pads may have a transitional portion between the cleansing portion and the gripping portion. The cleansing portion has a cleansing portion thickness Tc and a cleansing portion flexural rigidity Rc; and the gripping portion has a gripping portion thickness Tg and a gripping portion flexural rigidity Rg. The cleansing portion thickness Tc is at least about 10% greater than the gripping portion thickness Tg, and the cleansing portion flexural rigidity Rc is at least about 100% less than the gripping portion flexural rigidity Rg. The gripping portion has a distinct gripping edge. The gripping edges of the plurality of fibrous pads are separable from one another such that the gripping edges may be spaced apart for dispensing. Optionally, the plurality of pads may be compressed within the dispensing package.

22 Claims, 9 Drawing Sheets

FIBROUS PAD AND A DISPENSING PACKAGE THEREFOR

FIELD OF THE INVENTION

This invention relates to a fibrous pads package comprising a dispensing package and fibrous pads in combination. More particularly, this invention relates to a package of unconnected fibrous pads, such as cotton pads, each pad having a cleansing portion and a gripping portion.

BACKGROUND OF THE INVENTION

Fibrous pads are well known in the art. For example, fibrous pads are commonly used for applying and removing cosmetic substances and the like. Fibrous pads can also be used for medical purposes, or for wiping or cleaning tasks. Fibrous pads may have various shapes, such as circular, rectangular, etc., and may be supplied dry, with lotion, or moistened. To be widely consumer accepted, fibrous pads and their packaging must be disposable and inexpensive. In addition, they must be convenient to handle, i.e., when packed in a stack, the individual pads must be easily distinguishable and separable from one another and readily removable from the package.

Known in the art are the packages of pads interconnected in a stack such that withdrawal of one pad causes dislodging of the next pad. U.S. Pat. No. 4,159,772, issued on Jul. 3, 1979 to Harold Beck and assigned to Tissue Products, Co., Inc., Bronx, N.Y., discloses a pad dispensing device including a receptacle having a dispensing slot and a stack of pads within the receptacle. The pads are interconnected by elongated pull tabs having transverse lines of weakness at the junctions with the leading pads.

U.S. Pat. No. 4,927,064, issued on May 22, 1990 to Robert Burgin and assigned to IVF Maschinenfabrik Schaffhausen, Switzerland, discloses a stack of absorbent pads having opposed arcuate edges, overlaying each other in a dispensing container having a dispensing opening. Each pad is conjoined to the immediately adjacent pads by frangible bridge portions. The frangible bridge has a strength sufficient to dislodge the next pad, but insufficient to withdraw the pad completely before breakage of the bridge portion.

Unconnected fibrous pads are typically supplied in and dispensed from a dispensing package having a generally tube-like shape. Depending on the plan shape of the pads, such a dispensing package may have a cylindrical, rectangular, or other configuration. Usually, the dispensing package has an opening, typically at a top or a bottom, or a side wall near the top or the bottom, through which the pads can be removed by a user. The user has to insert her fingers through the dispensing opening, grasp a pad, and pull it out through the dispensing opening. The examples of such a dispensing package include the packages of cotton make up pads DEMAK'UP PERFECT® made by The Procter & Gamble Company; JOHNSON PURE COTTON made by Johnson & Johnson Consumer Products, Inc.; AKTIV PROFIL made by Jean Carol, Inc.; REVCO COSMETIC PAD distributed by Revco D.S., Inc.; COSME'PUF™ made by National Medical Patent, Inc.; SENTINEL'S BEST™ made by Sentinel Consumer Products, Inc.; WALGREENS QUILTED COTTON SQUARES distributed by Walgreen Co., Deerfield, Ill. 60015; ENVISION™ made for KMART Corporation, Troy, Mich. 48084; and KLEENEX BRAND® COTTON PAD made by Kimberly-Clark Corporation.

In all these examples, the pads are stacked inside a dispensing package. Dispensing packages (such as DEMAK 'UP, for example) may be hung up by a string such that the pads are stacked vertically. The bottom or the top of the package can then be partially opened to define a predetermined opening to expose the pads for their successive removal. In order to remove a single pad from the dispensing package, a consumer typically first has to distinguish between two or more abutting pads. However, because the pads, which are soft and fuzzy, are stacked in an abutting, face-to-face relationship with each other, there is no obvious separation of one pad from the next. Therefore, the removal of one individual pad at a time is difficult.

Therefore, it is an object of the claimed invention to provide a fibrous pad package of unconnected pads which are easily separable from one another by a consumer.

It is another object of the claimed invention to provide a stack of fibrous pads and a dispensing package in combination which would allow a consumer to easily remove an individual fibrous pad from the dispensing package.

It is still another object of the claimed invention to provide a fibrous pad having a cleansing portion and a gripping portion, the gripping portion having a thickness less than, and a flexural rigidity greater than those of the cleansing area.

It is a further object of the claimed invention to provide a fibrous pad package of compressed unconnected pads which are still easily separable from one another and removable from the package, despite the compression.

SUMMARY OF THE INVENTION

The invention comprises a fibrous pad package including a dispensing package and fibrous pads in combination. A lightweight dispensing package has a dispensing opening therein. A plurality of discrete fibrous pads is sequentially disposed in the dispensing package in an abutting relationship with each other. Each of the plurality of discrete fibrous pads has at least one cleansing portion and at least one gripping portion of predetermined size and shape. The cleansing portion has a cleansing portion thickness Tc and a cleansing portion flexural rigidity Rc. The gripping portion has a gripping portion thickness Tg and a gripping portion flexural rigidity Rg. The fibrous pad may also have a transitional portion between the cleansing portion and the gripping portion. The cleansing portion thickness Tc is at least about 50% greater than the gripping portion thickness Tg, and the cleansing portion flexural rigidity Rc is at least about 100% less than the gripping portion flexural rigidity Rg. In addition to being thinner and more rigid, the gripping portion has a distinct gripping edge associated with the gripping portion. When the plurality of the fibrous pads is disposed in the dispensing package, the gripping edges of the individual pads may be spaced apart from each other. Thus, the gripping edges are distinguishable and separable from one another for easy dispensing. The respective shapes of the cleansing and the gripping portions are designed such that, when used by a consumer, the pad, removed from the dispensing package, ordinarily bends along a bending axis, preferably located within the plan of the cleansing area. The bending axis has an associated bending distance of not less than about 0.3 inches. Optionally, the plurality of pads may be vertically compressed within the dispensing package up to about 50% the free height of the plurality.

BRIEF DESCRIPTION OF THE DRAWINGS

FIGS. 3A, 3B, 3C, 3D, 3E, 3F, 3G are top plan views of the different embodiments of the fibrous pad of the present invention, all having an arcuate overall shape, showing different shapes of a gripping portion G, a cleansing portion C, and a transitional portion B. FIGS. 3A-3E show the fibrous pads, each comprising one cleansing portion and one gripping portion.

DETAILED DESCRIPTION OF THE INVENTION

Figure 1A:
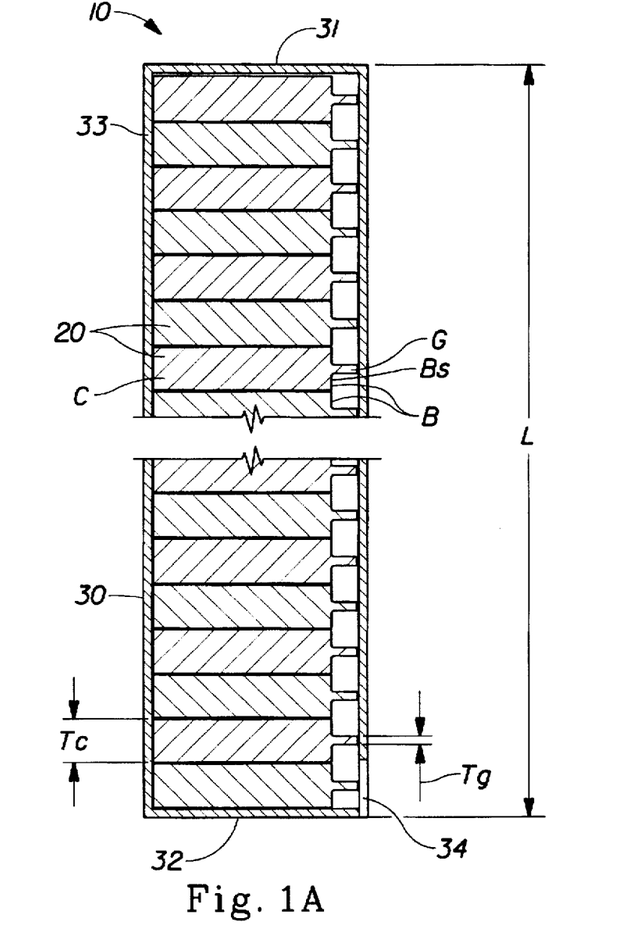
FIG. 1A is a side elevational view of a fibrous pads package of the present invention comprising a plurality of pads having gripping portions aligned vertically and separated from one another for easy dispensing.
Figure 1B:
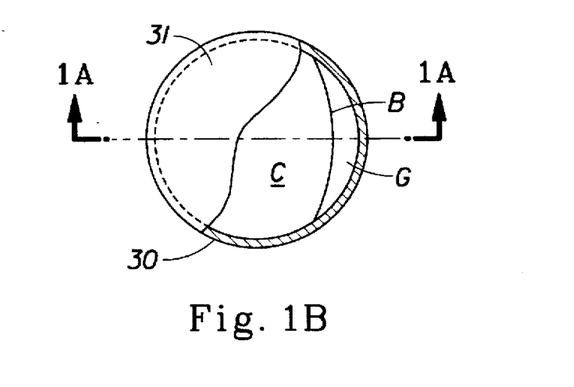
FIG. 1B is a plan view of a fibrous pad package of the present invention taken along the line 1B—1B and showing a fibrous pad having a cleansing portion C, a gripping portion G, and a transitional portion B therebetween.

Referring to FIG. 1A and 1B, a fibrous pads package 10 of the present invention includes a dispensing package 30 and fibrous pads 20 in combination. The dispensing package 30 shown in FIG. 1A has a first end 31, a second end 32, and at least one side wall 33 joined to the first end 31 and the second end 32. Preferably, the dispensing package 30 has an overall generally sleeve-type shape. The dispensing package 30 has a dispensing opening 34, preferably disposed near the first end 31 or the second end 32 of the dispensing package 30. The dispensing opening 34 may be disposed in the side wall 33, in the first end 31, or the second end 32 of the dispensing package 30. A line of weakness (not shown) may be provided to define the dispensing opening 34 and to facilitate opening of the dispensing package 30 along the line of weakness.

The dispensing package 30 is preferably made from a lightweight material, such as plastic. By "lightweight" it is meant that the dispensing package 30 is conventionally portable and does not have dead weight specifically added thereto. The dispensing package 30 can be either flexible or possess some rigidity. As used herein, the dispensing package is "flexible" if it is compliant and readily conforms to the contours of a stack of pads disposed inside the dispensing package 30. The preferred materials for the dispensing package 30 are polyethylene and thermoformed lightweight high density polyethylene (HDPE). However, other examples of lightweight materials, such as paper, paper board, polypropylene, lightweight foil, or mixtures thereof, may also be used for the dispensing package 30.

The dispensing package 30 may be either refillable or, preferably, disposable. By "disposable," it is meant that the dispensing package 30 is intended to be discarded after the plurality of pads 20 supplied therewith is depleted. The disposable dispensing package is not intended to be restocked with pads 20. Likewise, each pad 20 may be discarded after use, and is not intended to be laundered or otherwise restored. Alternatively, the dispensing package 30 may be refillable. By "refillable," it is meant that the dispensing package 30 is or may be restocked with the pads 20 after the initial supply of the pads 20 is depleted.

Figure 5:
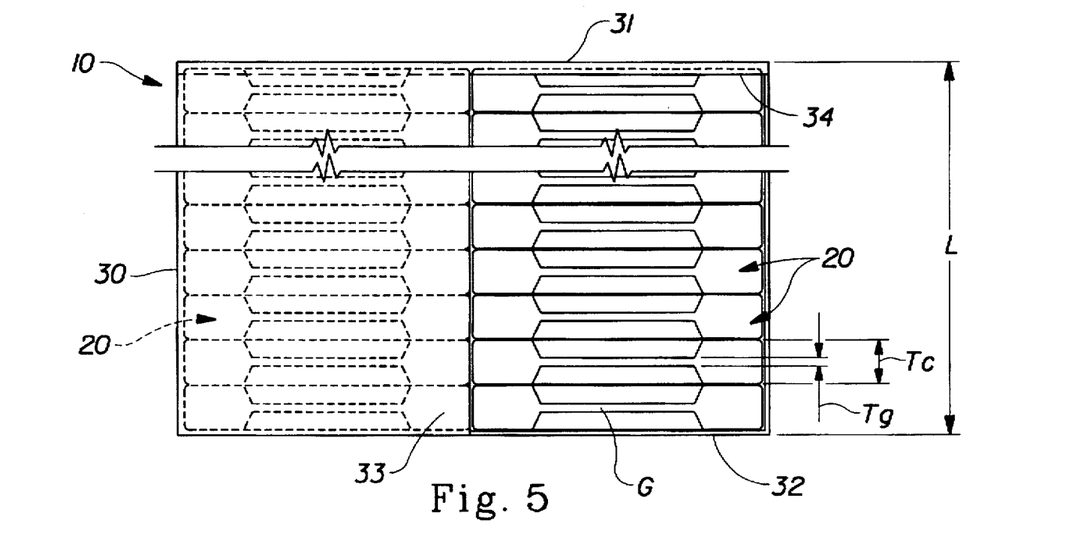
FIG. 5 is a side elevational view of a fibrous pads package of the present invention having a parallelepiped shape and comprising two pluralities of the fibrous pads, each plurality having gripping portions vertically aligned.
Figure 7:
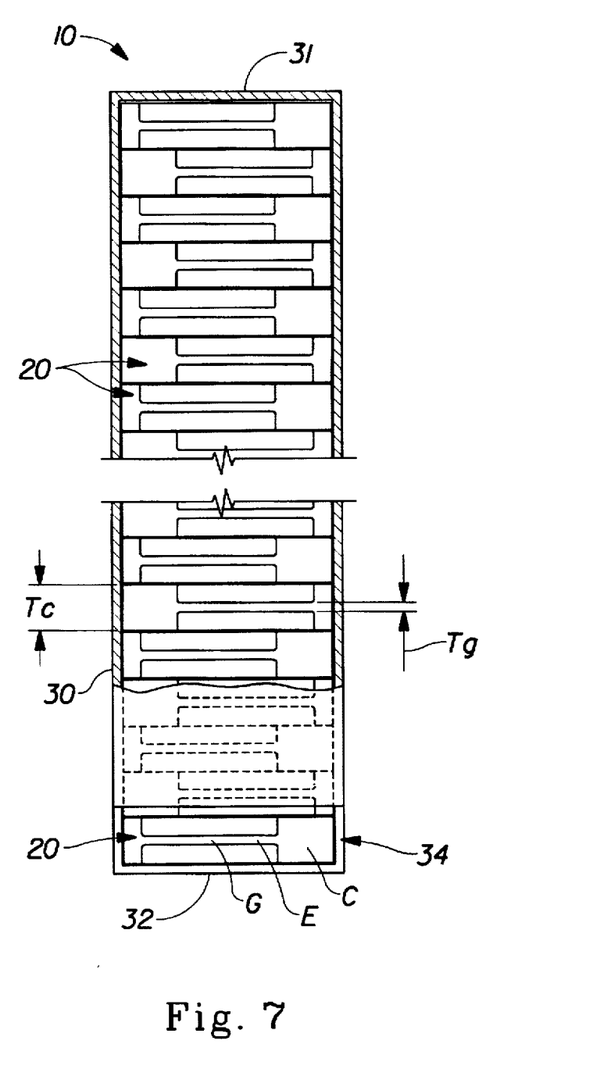
FIG. 7 is a side elevational view of a fibrous pads package of the present invention comprising a plurality of pads having gripping portions separated from each other for easy dispensing and disposed in the dispensing package in a vertically staggering, alternating pattern.

The fibrous pads 20 are sequentially disposed in an abutting, face-to-face, relationship with each other in the dispensing package 30. As used herein, the term "fibrous pad" or, simply, "pad" refers to a conventional hand-held implement that contains absorbent fibers made of cellulosic and synthetic material, or any combination thereof. Cotton and tree fibers are commonly used absorbent materials. The pads 20 may form one (FIGS. 1A and 7), two (FIG. 5), or more rows of stacked pads 20. As used herein, the term "plurality of fibrous pads 20" is synonymous to a row of stacked pads 20. Thus, FIGS. 1A and 7 show the package 10 of the present invention having one plurality of pads 20, while FIG. 5 shows the package 10 of the present invention having two pluralities of pads 20. One skilled in the art will readily understand that the present invention encompasses any number of the pluralities of fibrous pads 20 disposed in the dispensing package 30.

At least one plurality of discrete and unconnected fibrous pads 20 is sequentially disposed in an abutting relationship with each other in the dispensing package 30. As shown in FIGS. 1A and 7, one plurality of fibrous pads 20 is disposed in the dispensing package 30 having a generally tube-type shape. In the embodiment shown in FIG. 5, the dispensing package 30 is generally parallelepipedly shaped and has at least one generally planar wall 33 with a dispensing opening 34 therein. Preferably, two pluralities of fibrous pads 20 are disposed in the dispensing package 30 having a parallelepiped shape and shown in FIG. 5. Such a dispensing package having a parallelepiped shape, may be advantageously utilized for small-count packages or for packages comprising fibrous pads 20 having a generally rectangular shape, as shown in FIG. 5.

The unrestrained plurality of fibrous pads 20 has a free height. As used herein, the term "free height" refers to a vertical measurement, taken from a horizontal reference plane, of the plurality of pads 20, as it lays on the horizontal reference surface vertically unrestrained except for a minimal confining pressure of approximately 0.1 psi applied by a one-inch diameter pressure foot for five seconds. It is to be recognized that the same size and number of pads 20 comprising the plurality may have different free heights, depending primarily upon a caliper, or thickness, of the pads 20.

Referring now to FIG. 1A, the free height of the plurality of pads 20 may be equal to, greater, or less than a length L comprising a distance between the first end 31 and the second end 32 of the dispensing package 30, as shown in FIGS. 1A and 5. Preferably, the free height is equal to or greater than the length L of the dispensing package 30. If the free height is equal to or less than the length L, the plurality of pads 20 is said to be vertically unrestrained within the dispensing package 30. If the free height is greater than the length L, the plurality of pads 20 is vertically restrained, or compressed, within the dispensing package 30. The use of a compressed plurality of pads 20 is preferable because it allows to stack more pads 20 in the dispensing package 30 than it would be possible in the case of unrestrained plurality. Alternatively, the compressed plurality of pads 20 is preferable because it allows the use of smaller dispensing packages 30 receiving the same amount of pads 20 as in the case of the unrestrained plurality.

The term "vertical" designates the direction generally perpendicular to the plane of the pads 20. The term "vertical" is consistent with the arrangement of the drawings and is used herein for the convenience of describing the relative locations of the different elements of the package 10, without reference to gravity. One skilled in the art will readily understand that the package 10 of the present invention may be disposed and used such that the direction generally perpendicular to the plan of the pads 20 may have a position other than vertical.

The fibrous pad 20 of the present invention may have a variety of different shapes. The examples include, but are not limited to, circles and semi-circles, ellipsoids, polygons, etc., and any combinations thereof, which shapes are all included in the scope of the present invention. FIGS. 1A-3E and 6A-6C show the pads 20 having a generally arcuate shape, while FIG. 4A and 4B show the pads 20 having a generally polygonal shape.

Regardless of the shape, the fibrous pad 20 has a perimeter P, a first side 11 and a second side 12 opposite the first side 11. The individual fibrous pad 20 comprises at least two distinct portions: at least one cleansing portion C, and at least one gripping portion G of a predetermined size and shape. FIGS. 1B, 2B, 2D, 3A, 3B, 3D, 3E, 3F, 3G, 4B, 6A, 6B, 6C show various embodiments of the pad 20, all having the different shapes of their respective cleansing portions C and gripping portions G. As could be seen in these embodiments, the pad 20 may have a transitional portion B between the cleansing portion C and the gripping portion G.

The cleansing portion C has a first cleansing surface 21 and a second cleansing surface 22 opposite the first cleansing surface 21. The first cleansing surface 21 is disposed on and is a part of the first side 11 of the fibrous pad 20; and the second cleansing surface 22 is disposed on and is a part of the second side 12 of the fibrous pad 20. The first cleansing surface 21 and the second cleansing surface 22 of the same cleansing portion C need not be identical. For example, one of the cleansing surfaces 21 or 22 can be textured or otherwise treated. The textured cleansing surface of the cleansing portion C will be discussed below.

Figure 2A:
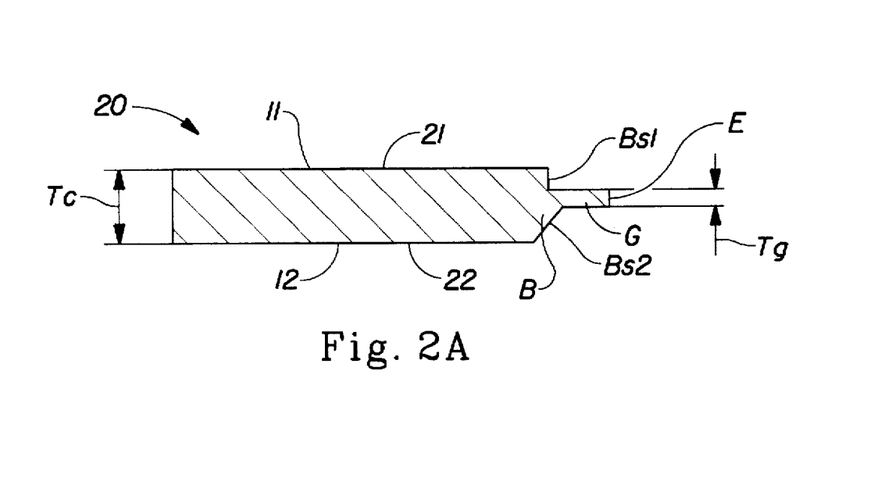
FIG. 2A is a side elevational view of an embodiment of the fibrous pad having a transitional portion B1 and a transitional portion B2 different from B1.
Figure 2B:
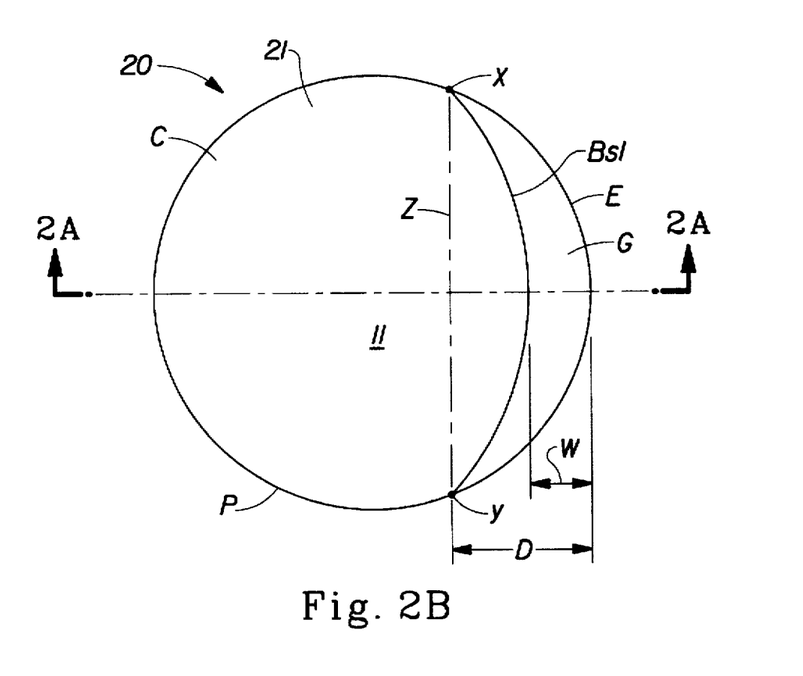
FIG. 2B is a top plan view of the fibrous pad shown in FIG. 2A.
Figure 2C:
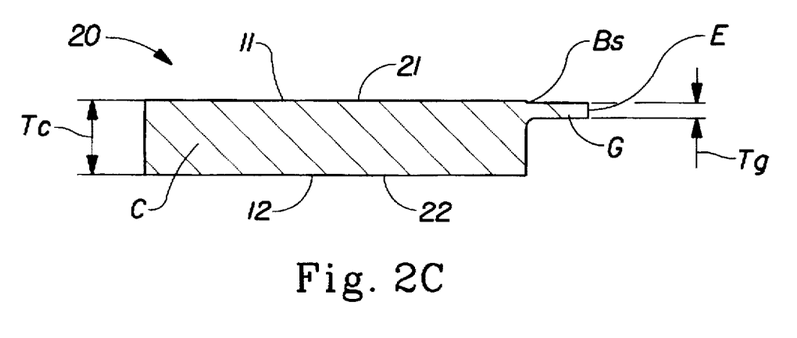
FIG. 2C is a side elevational view of a fibrous pad having a transitional portion Bs comprising a border line.
Figure 3A:
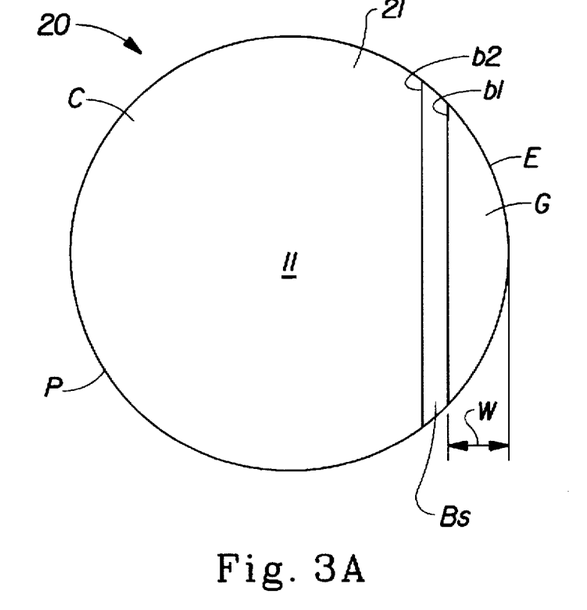
Figure 3B:
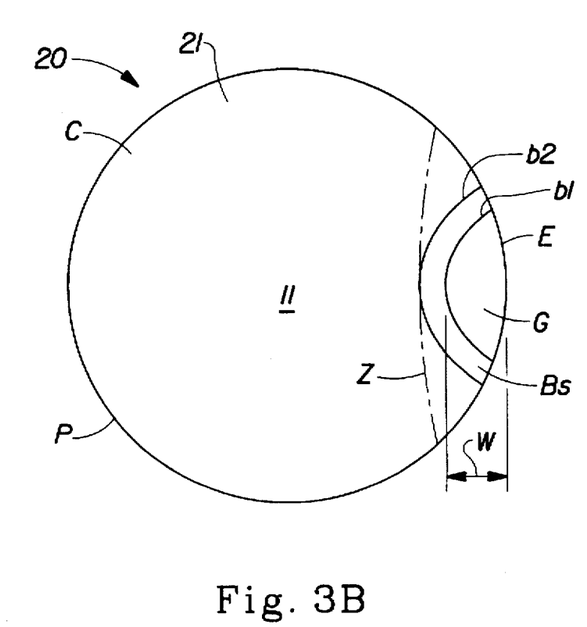

The first cleansing surface 21 and the second cleansing surface 22 define a cleansing portion thickness Tc of the pad 20, as best shown in FIGS. 2A and 2C. The preferred cleansing portion thickness Tc is between about 0.05 inches (1.27 mm) and about 1 inch (25.4 mm). More preferably, the cleansing portion thickness Tc is between about 0.1 inches (2.54 mm) and about 0.5 inches (12.7 mm). For the cotton pad 20 having its largest plan-view dimension (for example, a circular pad's diameter or a rectangular pad's longest side) of between about 2 inches (50.8 mm) and about 3 inches (76.2 mm), the most preferred cleansing portion thickness Tc is between about 0.15 (3.81 mm) and about 0.35 inches (8.89 mm). One skilled in the art will appreciate that the cleansing portion thickness Tc is arbitrary and may be chosen with regard to a variety of factors, such as: an intended use and type of a material of the pad 20, its overall dimensions and shape, the respective dimensions and shapes of the cleansing and gripping portions C and G, etc.

As used in this application, the cleansing portion thickness Tc is an average dimension computed as a result of an arithmetical division of the free height of a stack of at least ten fibrous pads 20 by the number of the pads 20 in the stack. It is to be understood that because the cleansing portions C of the plurality of pads 20 are soft and fuzzy and have a comparatively low density, the cleansing portion thickness Tc of the individual pads 20 disposed at and near the bottom of the vertical plurality may be slightly less than the cleansing portion thickness Tc of the individual pads 20 disposed at and near the top of the vertical plurality, due to a weight pressure of the stack. It should also be appreciated that in the pad 20 comprising more than one cleansing portion C (FIGS. 3F and 3G), the cleansing portions of the same pad 20 may have the different cleansing thicknesses Tc. Providing the pad 20 with two (or more) cleansing portions C, each cleansing portion C having its own cleansing portion thickness Tc different from the other's cleansing portion thickness Tc, may be beneficial when one of the cleansing portions is textured as discussed below.

The cleansing portion C has a cleansing portion flexural rigidity Rc. As used herein, the "flexural rigidity" is proportionate to the force which is necessary to bend, or flex, a structure, normal to its plane. The flexural rigidity of a particular structure equals the moment of inertia "I" of a cross-sectional portion of this structure multiplied by the modulus of elasticity "E" of this structure (i.e., the flexural rigidity equals R=IE). The flexural rigidity for simple structures can be theoretically derived, as described in elementary mechanics textbooks, such as one written by E. P. Popov, *Mechanics of Materials*, Second Edition, Prentice-Hall, Inc., Englewood Cliffs, N.J., 1976, incorporated by reference herein.

Figure 2D:
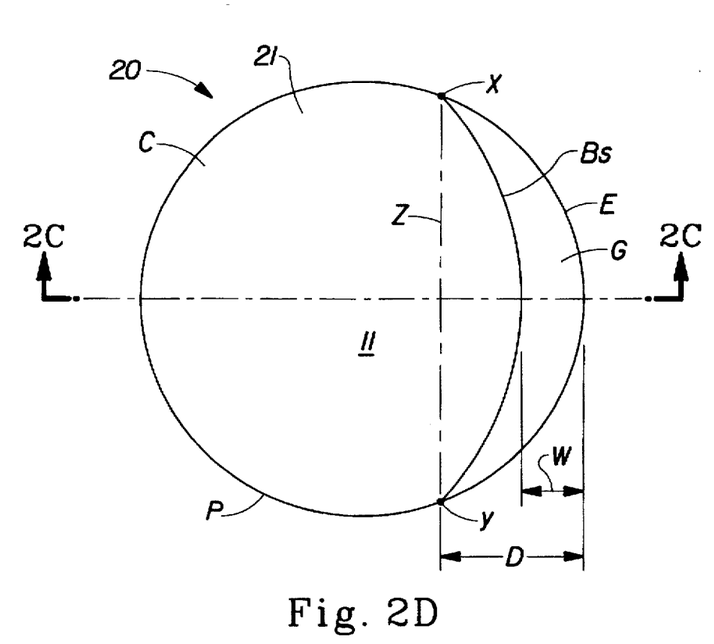
FIG. 2D is a top plan view of the pad shown in FIG. 2C.

The transitional portion B may have various shapes and may comprise at least one transitional surface Bs associated with one of the first side 11 or the second side 12 of the pad 20. FIGS. 3A and 3B show two different embodiments of the pad 20, each having the surface Bs defined by two lines b1 and b2. In some embodiments, the transitional surface Bs may be so narrow that, for all practical purposes, it comprises a border line between the cleansing portion C and the gripping portion G, as shown in FIGS. 2C and 2D.

The transitional surface Bs may have various positions relative to the first side 11 and the second side 12 of the pad 20. FIG. 2A shows the pad 20 having two transitional surfaces: Bs1 associated with the first side 11, and Bs2 associated with the second side 12 of the pad 20. As FIG. 2A shows, while the transitional surface Bs1 is generally vertical, the transitional surface Bs2 is not vertical. It should be carefully noted that in the plan view shown in FIG. 2B, the transitional surface Bs1 appears as a line.

Figure 6A:
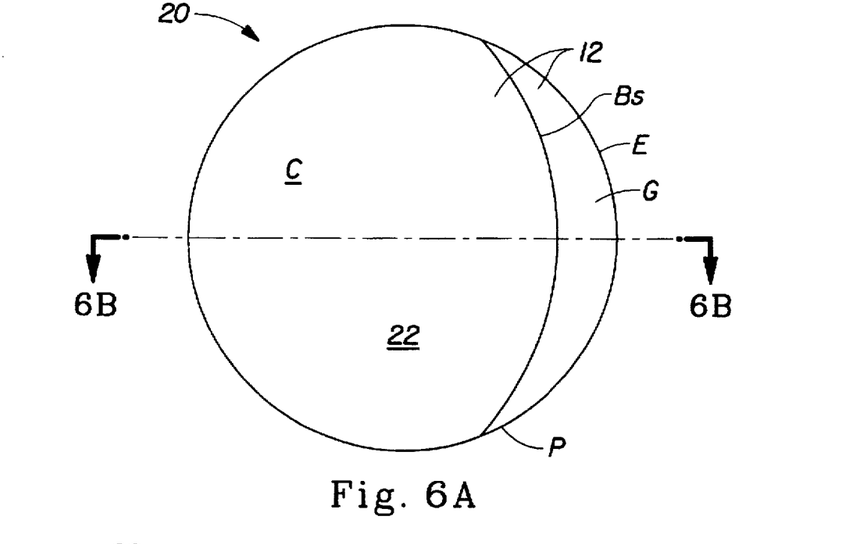
FIG. 6A is a bottom plan view of a pad having a gripping portion which includes a part of a cleansing portion.
Figure 6B:
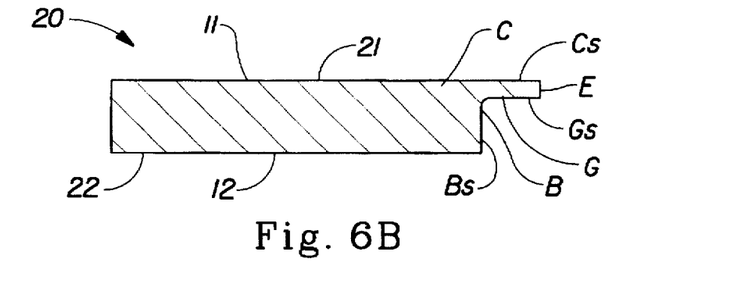
FIG. 6B is a side elevational view of the pad shown in FIG. 6A and taken along the line 6B—6B.
Figure 6C:
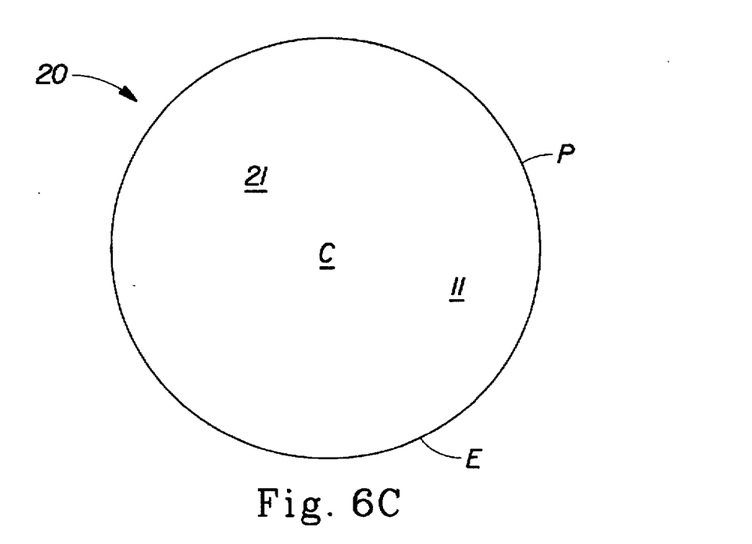
FIG. 6C is a top plan view of the pad shown in FIGS. 6A and 6B.

FIGS. 6A, 6B, 6C show still another embodiment of the pad 20. The transitional portion B of the pad 20 shown in FIGS. 6A, 6B, 6C has only one transitional surface Bs, which is associated with the second side 12 of the pad 20. In this embodiment, the entire first side 11 of the pad 20 may be said to be the first cleansing surface 21. Therefore, as could be seen in FIG. 6B, the gripping portion G has two opposite surfaces: a part Cs of the first cleansing surface 21 and a surface Gs of the gripping portion G. In this case, the gripping portion G comprises a part of the first cleansing surface 21.

As has been pointed out before, the transitional portion B (or its transitional surface or surfaces Bs) may have various plan view configurations, depending on the respective shapes of the cleansing portion C and the gripping portion G of the pad 20. Preferably, the transitional portion B intersects the perimeter P of the pad 20 in at least two opposite points (x and y in the plan view of FIG. 2B). Preferably, the cleansing portion C and the gripping portion G each comprises a part of the perimeter P of the fibrous pad 20. That is to say, the cleansing portion C is juxtaposed with at least a part of the perimeter P, and the gripping portion G is juxtaposed with at least a part of the perimeter P of the fibrous pad 20.

The gripping portion G has a gripping portion thickness Tg, and a gripping portion flexural rigidity Rg. The gripping portion thickness Tg is less than the cleansing portion thickness Tc, and the gripping portion flexural rigidity Rg is greater than the cleansing portion flexural rigidity Rc. A commercially available instrument called a Dynamic Mechanical Analyzer (DMA), Model 7 Series/UNIX DMA7, made by Perkin-Elmer Corporation, Mail Station 131, 761 Main Avenue, Nowalk, Conn. 06859-9966, has been used to determine the gripping portion flexural rigidity Rg of the pads 20 of the present invention. The equipment and the test steps are described below.

As has already been pointed out, in the present application, the references to the cleansing portion thickness Tc and the gripping portion thickness Tg are made with regard to the vertically unrestrained plurality of pads 20. One skilled in the art will readily understand that a vertical restraint will reduce the cleansing portion thickness Tc. The preferred gripping portion thickness Tg is between about 0.005 inches (0.127 mm) and about 0.5 inches (12.7 mm). More preferably, the gripping portion thickness is between about 0.02 inches (0.5 mm) and about 0.2 inches (5.88 mm). For the cotton pad 20 having its largest plan-view dimension of between about 2 inches (50.8 mm) and about 3 inches (76.2 mm), the most preferred gripping portion thickness is about 0.06 inches (1.524 mm). The gripping portion thickness Tg is measured using a Vernier caliper guage, such as Digit-Cal MKIV Caliper guage, made by Brown & Sharpe Manufacturing Company, Precision Park, 200 French Town Road, North Kingstown, R.I. 02825.

For a consumer, to be able to distinguish between individual pads 20 comprising the plurality, the gripping portion G must be appreciably thinner than the cleansing portion C of the pad 20. The fibrous pad 20 of the present invention has the cleansing portion thickness Tc at least about 50% greater than the gripping portion thickness Tg. Preferably, the cleansing portion thickness Tc is at least about 100% greater than the gripping portion thickness Tg. More preferably, the cleansing portion thickness Tc is at least about 200% greater than the gripping portion thickness Tg. Most preferably, the cleansing portion thickness Tc is at least about 300% greater than the gripping portion thickness Tg.

In addition to being thinner than the cleansing portion C, the gripping portion G is more rigid than the cleansing portion C. The flexural rigidity Rg of the gripping portion G is at least 100% greater than the flexural rigidity Rc of the cleansing portion C. Preferably, the flexural rigidity Rg of the gripping portion G is at least about 500% greater than the flexural rigidity Rc of the cleansing portion C. More preferably, the flexural rigidity Rg of the gripping portion G is at least about 1000% greater than the flexural rigidity Rc of the cleansing portion C. The Dynamic Mechanical Analyzer (DMA) described hereabove was used to measure the gripping portion flexural rigidity Rg.

For the purposes of this application, the samples of the DEMAK'UP® pads having an initial thickness (cleansing portion thickness Tc) of between 0.19 inches (4.9 mm) and 0.2 inches (5.08 mm) were used. Using these samples, two test groups of the "gripping portions" were created: a test group #1 created by embossing the samples under approximately 4890 pounds per square inch (psi), and a test group #2 created by embossing the samples under approximately 2450 psi. The embossing was performed using a standard eight-inch diameter cylinder air press. A matched steel die set was affixed to the press which contains a regular pyramidal pattern on the surfaces of the dies. The heights of the pyramids were about 0.38 inches (9.65 mm) with all walls at a 45-degree angle. The two dies were positioned so that they would interlock together when the press is activated.

In each test group, five rectangular samples, each having a size of approximately 0.590 inches (15 mm)×0.197 inches (5 mm), were prepared. Each sample was cut either manually with a razor blade, or cutting die. At least ten minutes were allowed for the samples to recover from any compression associated with the cutting, before their plan view dimensions and thickness (Tg) were measured with the RAM Optical Measurement Inspection System II (OMIS II) made by RAM Optical Instrumentation, Inc., 15192 Triton Lane, Huntington Beach, Calif. 92649. Then, each sample was analyzed using a scaled-down modification of the three-point bend test in the frequency scan mode of the DMA7, over the range of 0.1 to 20 Hz. The three-point test is described in ASTM, Designation: D 5023- 95a, *Standard Test Method for Measuring the Dynamic Mechanical Properties Of Plastics Using Three Point Bending*, Published December 1995, which description is incorporated herein by reference. An appropriate static force, ranging from 1000 Pa to 10000 Pa, and a dynamic force equal about 80% the static force, were programmed into the method.

Each sample was centered on the loading platform such that the sample's longest dimension was located across the bending platform, the probe was lowered to rest firmly on the top of the sample, and the test was started. The DMA software reports a storage modulus. The storage modulus then is multiplied by the moment of inertia "I" to yield the flexural rigidity "R." The moment of inertia is calculated as $I=bd^3/12$, where "b" is a span width of the tested sample; and "d" is a thickness of the tested sample.

Several pad samples of the prior art containing compressed portions were tested. The span width "b" was selected b=2.5 mm for the tested compressed portions of the prior art samples. For the samples of the present invention, the span width "b" was selected b=5.0 mm because the tested samples of the present invention were considerably thicker than the tested samples of the prior art. (The span "b" is selected to be at least about 3 times greater than the thickness of the tested sample.) The results of the tests are shown in the following TABLE.

TABLE

| Material/Source | Number of Samples Tested | Thickness, Average (meters) | Flexural Rigidity, Average (Newton-meters$^2$) |
| --- | --- | --- | --- |
| Johnson Pure Cotton | 2 | $3.25 \times 10^{-4}$ | $2.30 \times 10^{-7}$ |
| Aktiv Profil | 2 | $3.07 \times 10^{-4}$ | $8.90 \times 10^{-8}$ |
| Envision | 2 | $2.88 \times 10^{-4}$ | $1.00 \times 10^{-7}$ |
| Walgreens | 2 | $2.40 \times 10^{-4}$ | $9.30 \times 10^{-8}$ |

TABLE-continued

| Material/Source | Number of Samples Tested | Thickness, Average (meters) | Flexural Rigidity, Average (Newton-meters$^2$) |
|---|---|---|---|
| Invention (4890 psi) | 5 | $1.00 \times 10^{-3}$ | $5.90 \times 10^{-7}$ |
| Invention (2450 psi) | 5 | $1.60 \times 10^{-3}$ | $4.30 \times 10^{-7}$ |

While not intended to be bound by theory, the applicants believe that when the pad 20 is used by a consumer, the difference in the flexural rigidities Rg and Rc causes the pad 20 to ordinarily bend through the cleansing portion C, as a portion of less flexural resistance, along a bending axis Z. As used herein, the term "bending axis Z" designates an imaginary line about which the pad 20 naturally bends when dispensed or used by a consumer who holds the pad 20 by a gripping portion G. The bending axis Z is schematically indicated in FIGS. 2B, 2D, 3B as a dashed line. It is to be understood that although in FIGS. 2B, 2D, 3B the bending axis Z is shown as a straight line, the bending axis Z may comprise a non-straight (for example, curved, or undulated) line—due to the softness and possible permutations of consistency/density of the cleansing portion C of the pad 20. It should also be understood that the pad 20 can be easily forced to bend practically along any line within an overall shape of the pad 20, without regard to comparative rigidities Rc and Rg. The axis Z merely indicates the preferred and most probable or natural bending line of the pad 20.

Preferably, each gripping portion G has a distinct gripping edge E associated with each gripping portion G. As shown in FIGS. 2B, 2D, 3A, 3B, 3D, 3E, 3F, 3G, 4B, 6B, the gripping edge E comprises a part of the perimeter P of the pad 20. Preferably, the gripping edge E comprises the same part of the perimeter P which is juxtaposed with the gripping portion G. The gripping edge E is an individually-distinct selvage, preferably finished such that it minimizes or eliminates raveling of the fibers at and near the gripping edge E. The gripping edge E is preferably more rigid than the part of the perimeter P juxtaposed with the cleansing portion C. As shown in FIGS. 1A and 5, when the pads are vertically stacked in the dispensing package 12, the gripping edges E of the individual pads 20 are separable from one another such that the gripping edges E of the individual pads 20 may be spaced apart for easy dispensing. A consumer, using her fingers, can easily, first—distinguish the individual pad 20 by "feeling" this pad's gripping edge E, and, second—grasp the gripping portion G and pull the individual pad 20 out of the stack of pads.

Preferably, the bending axis Z has a bending distance D associated with the bending axis Z. As used herein, the term "bending distance D" indicates the maximal distance, measured as perpendicular to the bending axis Z, between the corresponding gripping edge E and the bending axis Z of the pad 20. FIGS. 2B, 2D, 3D, 3E illustrate what is meant by the "bending distance D." The bending distance D should be long enough to allow a consumer to comfortably hold and manipulate the pad 20, and should not be less than about 0.3 inches (7.62 mm). The preferred bending distance D is between about 0.4 inches (10.6 mm) and about 2.0 inches (50.8 mm). The more preferred bending distance D is between about 0.5 inches (12.7 mm) and about 1.5 inches (38.1 mm). The bending distance D defined hereabove might not be applicable to the pad 20 comprising more than one cleansing portion C and/or more than one gripping portion G shown in FIGS. 3F and 3G.

Each gripping portion G has a gripping portion width W. As used herein, the term "gripping portion width" means the maximal distance between the gripping edge E of the gripping portion G and the opposite side of the same gripping portion G, measured perpendicular relative to the gripping edge E (or, if the gripping edge is curved, perpendicular to the tangent of the gripping edge). In other words, the "gripping portion width" W of the gripping portion G is its greatest inboard dimension measured perpendicular to the gripping edge E. FIGS. 2B, 2D, 3A, 3B, 4B illustrate what is meant by the gripping portion width W. The gripping portion width W of the pad 20 of the present invention is not less than 0.25 inches (6.35 mm). For the cotton pad 20 having its largest plan-view dimension of between about 2 inches (50.8 mm) and about 3 inches (76.2 mm), the preferred gripping portion width W is not less than about 0.3 inches (7.62 mm).

The respective shapes of the gripping portion G and the cleansing portion C of the pad 20 of the present invention can be advantageously designed such that the bending axis Z lies within the cleansing portion C. FIGS. 2B and 2D show the gripping portion G having a "crescent" or "moon-like" shape. This crescent shape allows to maximize the cleansing area C of the pad 20 and, at the same time, make the gripping area G, having the associated gripping edge E, large enough to allow a consumer to easily distinguish and grasp the individual pad 20 in the stack. While the crescent shape of the gripping portion G of the pad 20 is preferred, other embodiments of the gripping portion G are possible. FIGS. 3A, 3B, 3F, 3G, 4B show various shapes of the gripping portion(s) G of the pad 20 of the present invention, which are intended to be neither all-inclusive nor exhaustive examples of the possible shapes of the gripping area G.

Both the difference in the respective thicknesses Tc and Tg, and the difference in the respective rigidities Rg and Rc may be created by densification of an integral portion of a generally homogeneous pad comprising only a cleansing portion, thus creating an integral gripping portion G. Mechanical embossing is one preferred method of creating an integral gripping portion G of the pad 20. Also, the integral gripping portion G may be formed by thermoplastic embossing. The gripping portion is "integral" when it is an inherent part of the pad 20, i.e., is formed from the same piece of a material from which the cleansing portion C is formed. Embossing (either mechanical or thermoplastic) can be made an integral part of a cutting operation, if the pads 20 are formed by cutting the individual pads from a fibrous sheet. The gripping portion G can also be formed by hydrogen bonding, thermoplastic embossing, air pressurizing, or any other method known in the art, which method would produce the gripping portion G being appreciably thinner and more rigid than the cleansing portion C. Preferably, the gripping edge E can also be formed incidentally to and as an integral part of forming the gripping portion G. Alternatively, the gripping edge E can be specially treated after the gripping portion G has been formed. The other methods by which the gripping edge E can be formed include, but are not limited to, thermal and thermoplastic treatment, adhesive or glue application, hydrogen bonding, etc., and any combinations thereof.

Embossing can be accomplished according to U.S. Pat. No. 3,414,459, issued Dec. 3, 1968 to Wells and commonly assigned; U.S. Pat. No. 3,547,723 issued on Dec. 15, 1979 to Gresham; U.S. Pat. No. 3,556,907 issued on Jan. 19, 1971 to Nystrand; U.S. Pat. No. 3,708,366 issued on Jan. 2, 1973 to Donnelly; U.S. Pat. No. 3,738,905 issued on Jan. 12, 1973 to Thomas;. U.S. Pat. No. 3,867,225 issued on Feb. 18, 1975 to Nystrand; U.S. Pat. No. 4,483,728 issued on Nov. 20, 1984 to Bauernfeind; U.S. Pat. No. 5,294,475 issued on Mar.

15, 1994 to McNeil and commonly assigned, which patents are incorporated by reference herein.

Although not preferred, the gripping portion G may be formed from a separate piece of a material and independently from forming the cleansing portion C, and then attached to the cleansing portion C. As used herein, such a gripping portion is an "adjacent" gripping portion. The adjacent gripping portion G can be secured to the cleansing portion C in any of several ways known in the art, such as by ultrasonic bonding, heat/pressure sealing, or bonding the adjacent gripping portion G and the cleansing portion C using adhesives or glues known in the art. The adjacent gripping portion G and the cleansing portion C may comprise the same material. Alternatively, the adjacent gripping portion G may comprise a material different from that of the cleansing portion C.

Figure 3C:
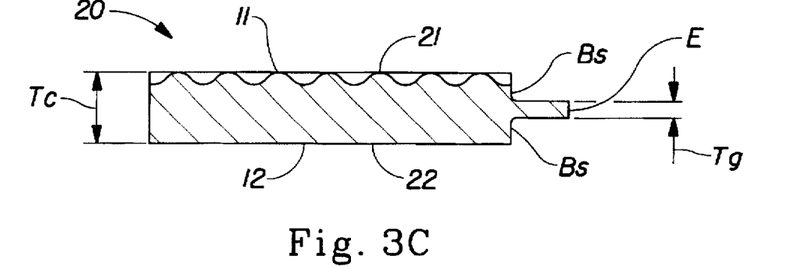
Figure 3D:
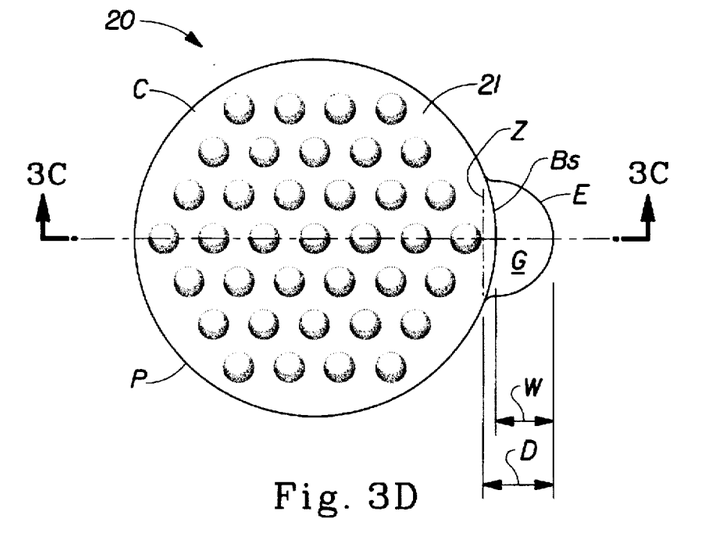
Figure 3E:
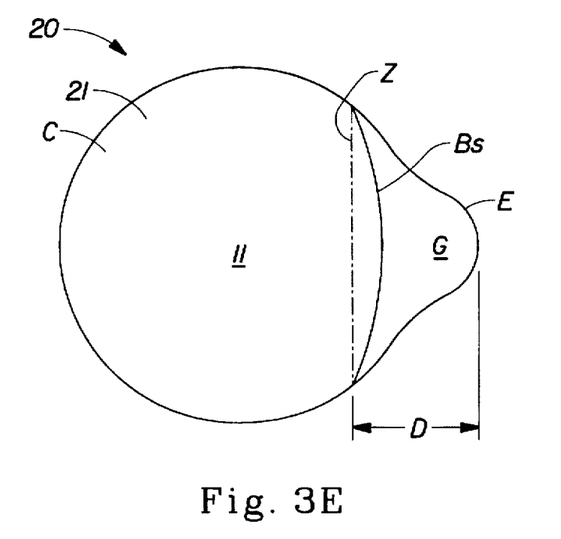
Figure 3F:
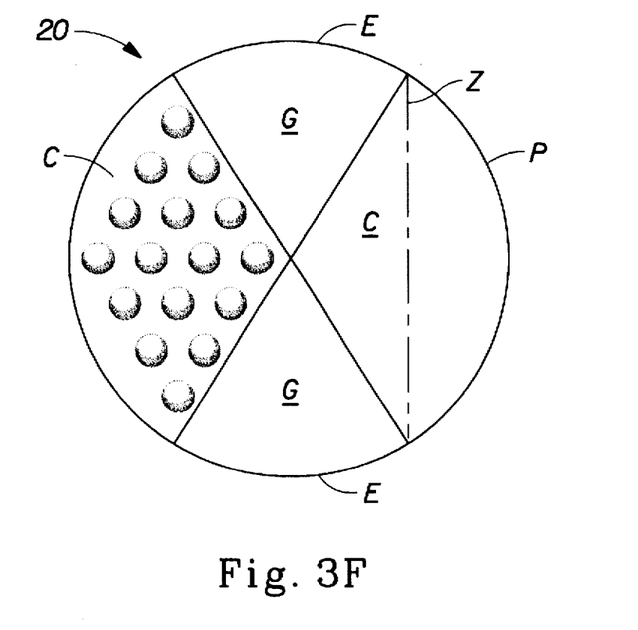
FIG. 3F shows the pad comprising two cleansing portions and two gripping portions.
Figure 3G:
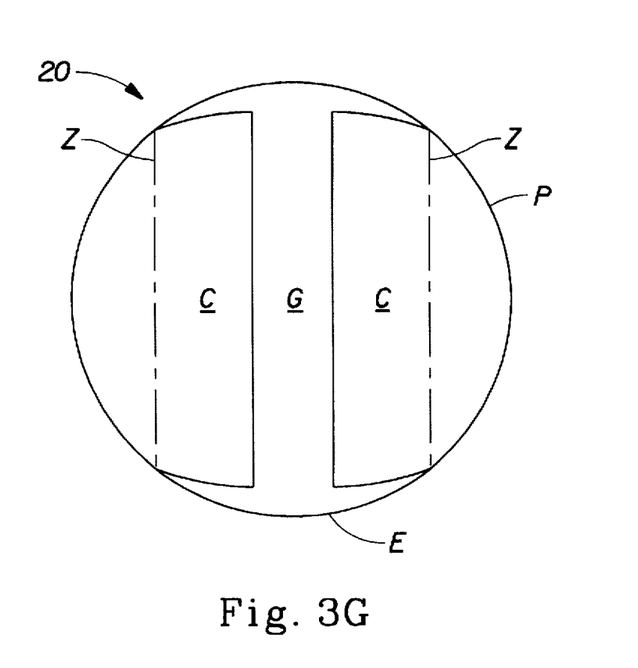
FIG. 3G shows the pad comprising two cleansing portions and one gripping portion.
Figure 4A:
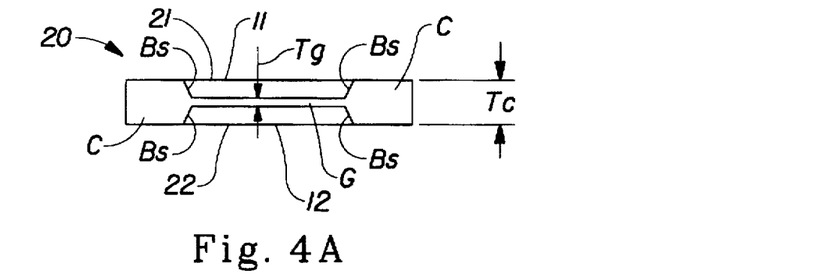
FIG. 4A is a side elevational view of a fibrous pad of the present invention having a polygonal overall shape.
Figure 4B:
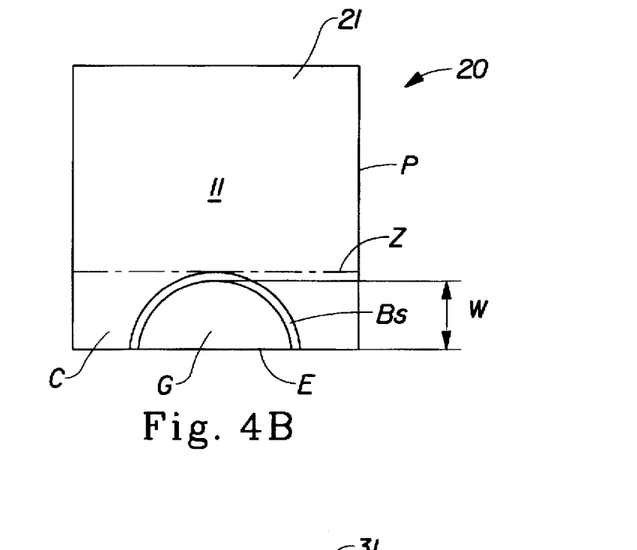
FIG. 4B is a top plan view of the pad shown in FIG. 4A.

Referring now to FIG. 3C, the first cleansing surface 21 and/or the second cleansing surface 22 may be textured or have a textured area. As used herein, the term "textured area" refers to the characteristic of the first cleansing surface 21 and/or second cleansing surface 22 of the fibrous pad 20, created by discontinuities or non-planar interruptions in what would ordinarily be a generally smooth or planar surface. These discontinuities or non-planar interruptions can comprise projections from or depressions in such a smooth surface. The textured surface is believed to facilitate the removal of cosmetic substances, dirt and the like from one's face or body. The textured surface can also be advantageously utilized in the pad 20 designed for the cleaning and wiping purposes. FIGS. 3C and 3D show one type of the textured surface that can be provided in accordance with the present invention. FIG. 3F shows the pad 20 having only the surface of one of the two cleansing portions C is textured. Of course, the pad 20 can have the first and/or second cleansing surface 21, 22 which is/are only partially textured. It should be understood that neither the particular type nor the particular shape of the textured surface shown in FIGS. 3C, 3D and 3F are all-inclusive or exhaustive examples of the textured surface that can be utilized in the pads 20 of the present invention. The textured surface shown in FIGS. 3C and 3D can be formed by embossing, or any other suitable method known in the art, and be incidental to forming the pad 20 and/or the gripping area G.

Referring back to FIGS. 1A, 5, 7, the plurality of pads 20 is disposed in the dispensing package 30 such that the position of the gripping areas G correlates with the position of the dispensing opening 34. Therefore, the gripping portion G, by virtue of being thinner and more rigid than the cleansing portion C, and having a distinct rigid gripping edge E, allows a consumer, using a tactile sensation, to more easily distinguish between the individual pads 20 inside the dispensing package 30. In addition, the gripping portion G provides a convenient thumb and finger hold which facilitates the removal of the individual pad 20 from the dispensing package 30 through the dispensing opening 34. The plurality of pads 20 can be disposed in the dispensing package 30 such that the gripping portions G are vertically aligned with each other and with the dispensing opening 34, as shown in FIG. 1A. Alternatively, the plurality of pads 20 can be disposed in the dispensing package 30 such that the gripping portions G comprise an alternating, vertically staggering, pattern (FIG. 7), or a random pattern (not shown), relative to the central vertical axis of the package 10. Still, in both latter cases, the gripping portions should preferably be generally aligned with the dispensing opening 34.

The fibrous pads 20 of the present invention may be advantageously used if the stack of pads 20 is compressed within the dispensing package 30. The pads of the prior art are difficult to individually distinguish in a stack even if the stack is not compressed. The task of distinguishing and removing the individual pads of the prior art from the stack becomes even more difficult, if not impossible, when the stack is compressed. In the compressed stack, the pads of the prior art become virtually indistinguishable from one another. In a sharp contrast, the pads 20 of the present invention comprising a compressed plurality retain the ability to be easily distinguished from one another and individually removed from the plurality—due to the existence of the gripping portion G having the gripping edge E. The plurality of pads 20 of the present invention may be advantageously compressed up to about 50% the free height, without loosing the benefits, described hereabove, over the prior art.

What is claimed is:

1. A fibrous pads package including a dispensing package and fibrous pads in combination, said fibrous pads package comprising:
   a lightweight dispensing package having a dispensing opening therein; and
   a plurality of discrete fibrous pads sequentially disposed in said dispensing package in an abutting relationship with each other, each of said plurality of discrete fibrous pads comprising:
      at least one cleansing portion having a cleansing portion thickness Tc and a cleansing portion flexural rigidity Rc, and
      at least one gripping portion of predetermined size and shape, said at least one gripping portion having a gripping portion thickness Tg, a gripping portion flexural rigidity Rg, and a gripping portion width W of not less than 0.25 inches,
   said cleansing portion thickness Tc being at least about 50% greater than said gripping portion thickness Tg, and
   said cleansing portion flexural rigidity Rc being at least about 100% less than said gripping portion flexural rigidity Rg,
   said at least one gripping portion of each of said plurality of discrete fibrous pads having a gripping edge associated with said at least one gripping portion, said gripping edges being separable from one another such that said gripping edges can be spaced apart for dispensing.

2. The package according to claim 1, wherein said gripping portion thickness Tg is between 0.005 inches and 0.5 inches.

3. The package according to claim 2, wherein said gripping portion thickness Tg is between 0.02 inches and 0.2 inches.

4. The package according to claim 3, wherein said gripping portion flexural rigidity Rg is at least $4.5 \times 10^{-7}$ N-M$^2$.

5. The package according to claim 4, wherein said at least one gripping portion and said at least one cleansing portion form a bending axis having a bending distance of not less than 0.3 inches.

6. The package according to claim 5, wherein said bending axis has a bending distance of between 0.4 inches and 2.0 inches.

7. The package according to claim 1, wherein said dispensing package comprises polyethylene.

8. The package according to claim 1, wherein said fibrous pad further comprises a transitional portion between said at least one cleansing portion and said at least one gripping portion.

9. A fibrous pads package including a dispensing package and fibrous pads in combination, said fibrous pads package comprising:
- a lightweight dispensing package having a dispensing opening therein; and
- a plurality of discrete fibrous pads sequentially disposed in said dispensing package in an abutting relationship with each other, each of said plurality of discrete fibrous pads comprising:
  - at least one cleansing portion having a cleansing portion thickness Tc and a cleansing portion flexural rigidity Rc;
  - at least one gripping portion of predetermined size and shape, said gripping portion having a gripping portion thickness Tg and a gripping portion flexural rigidity Rg; and
  - a transitional portion disposed between said at least one cleansing portion and said at least one gripping portion,
  - said cleansing portion thickness Tc being about 50% greater than said gripping portion thickness Tg, and
  - said cleansing portion flexural rigidity Rc being about 100% less than said gripping portion flexural rigidity Rg,
  - said at least one gripping portion of each of said plurality of discrete fibrous pads having a gripping edge associated with said at least one gripping portion, said gripping edges being separable from one another such that said gripping edges can be spaced apart for dispensing.

10. A fibrous pads package including a dispensing package and fibrous pads in combination, said fibrous pads package comprising:
- a lightweight dispensing package having a dispensing opening therein; and
- a plurality of discrete fibrous pads sequentially disposed in said dispensing package in an abutting relationship with each other,
- each of said plurality of discrete fibrous pads comprising:
  - a cleansing portion having a cleansing portion thickness Tc and a cleansing portion flexural rigidity Rc, and
  - a gripping portion of predetermined size and shape, said gripping portion having a gripping portion thickness Tg less than said cleansing portion thickness Tc, and a gripping portion flexural rigidity Rg greater than said cleansing portion flexural rigidity Rc,
  - said cleansing portion and said gripping portion forming a bending axis having a bending distance of not less than 0.3 inches, each of said plurality of discrete fibrous pads being bendable along said bending axis when said fibrous pad is used,
  - said gripping portion of each of said plurality of discrete fibrous pads having a gripping edge associated with said gripping portion, said gripping edges being separable from one another such that said gripping edges can be spaced apart for dispensing.

11. A fibrous pads package including a dispensing package and fibrous pads in combination, said fibrous pads package comprising:
- a lightweight dispensing package having a dispensing opening therein; and
- a plurality of discrete fibrous pads sequentially disposed in said dispensing package in an abutting relationship with each other, each of said plurality of discrete fibrous pads having a perimeter and comprising:
  - at least one cleansing portion juxtaposed with at least a part of said perimeter and having a cleansing portion thickness Tc and a cleansing portion flexural rigidity Rc, and
  - at least one gripping portion of predetermined size and shape, said at least one gripping portion being juxtaposed with at least a part of said perimeter, said at least one gripping portion having a gripping portion thickness Tg and a gripping portion flexural rigidity Rg,
  - said cleansing portion thickness Tc being at least about 50% greater than said gripping portion thickness Tg, and
  - said cleansing portion flexural rigidity Rc being at least about 100% less than said gripping portion flexural rigidity Rg,
  - said at least one gripping portion of each of said plurality of discrete fibrous pads having a gripping edge associated with said at least one gripping portion, said gripping edges being separable from one another such that said gripping edges can be spaced apart for dispensing.

12. The pad as in claim 1, 10 or 11, further comprising said plurality of discrete fibrous pads vertically compressed.

13. A fibrous pad comprising:
- at least one cleansing portion having a cleansing portion thickness Tc and a cleansing portion flexural rigidity Rc, and
- at least one gripping portion of predetermined size and shape, said at least one gripping portion including a gripping edge associated with said at least one gripping portion, said at least one gripping portion having a gripping portion thickness Tg, a gripping portion flexural rigidity Rg, and a gripping portion width W of not less than 0.25 inches,
- said cleansing portion thickness Tc being at least about 50% greater than said gripping portion thickness Tg, and
- said cleansing portion flexural rigidity Rc being at least about 100% less than said gripping portion flexural rigidity Rg,
- said at least one cleansing portion further having a first cleansing surface and a second cleansing surface opposite said first cleansing surface.

14. The pad according to claim 13, wherein said gripping portion thickness Tg is between 0.005 inches and 0.5 inches.

15. The pad according to claim 14, wherein said gripping portion thickness Tg is between 0.02 inches and 0.2 inches.

16. The pad according to claim 15, wherein said gripping portion flexural rigidity Rg is at least $4.5 \times 10^{-7}$ N-M$^2$.

17. The pad according to claim 13, wherein at least part of said first cleansing surface is textured.

18. The pad according to claim 17, wherein at least part of said second cleansing surface is textured.

19. The pad according to claim 13, wherein said at least one gripping portion comprises a part of said first cleansing surface or said second cleansing surface.

20. A fibrous pad having a perimeter and comprising:
- at least one cleansing portion juxtaposed with at least a part of said perimeter and having a cleansing portion thickness Tc and a cleansing portion flexural rigidity Rc, and
- at least one gripping portion of predetermined size and shape, said gripping portion being juxtaposed with at least a part of said perimeter and having a gripping portion thickness Tg and a gripping portion flexural rigidity Rg, said at least one gripping portion including a distinct gripping edge associated with said at least one gripping portion, said cleansing portion thickness Tc being at least about 50% greater than said gripping portion thickness Tg, and said cleansing portion flexural rigidity Rc being at least about 100% less than said gripping portion flexural rigidity Rg, said cleansing portion further having a first cleansing surface and a second cleansing surface opposite said first cleansing surface.

21. The pad according to claims 13 or 20, wherein said fibrous pad further comprises a transitional portion between said at least one cleansing portion and said at least one gripping portion.

22. A fibrous pad comprising:

a cleansing portion having a cleansing portion thickness Tc and a cleansing portion flexural rigidity Rc, and a gripping portion of predetermined size and shape, said gripping portion having a gripping portion thickness Tg less than said cleansing portion thickness Tc, and a gripping portion flexural rigidity Rg greater than said cleansing portion flexural rigidity Rc, said gripping portion further having a gripping edge associated with said gripping portion, said cleansing portion and said gripping portion forming a bending axis having a bending distance of not less than 0.3 inches, each of said plurality of discrete fibrous pads being bendable along said bending axis when said fibrous pad is used.

* * * * *